United States Patent
Stamler et al.

(10) Patent No.: US 6,472,390 B1
(45) Date of Patent: Oct. 29, 2002

(54) USE OF THERAPEUTIC DOSAGES FOR NITRIC OXIDE DONORS WHICH DO NOT SIGNIFICANTLY LOWER BLOOD PRESSURE OR PULMONARY ARTERY PRESSURE

(75) Inventors: Jonathan S. Stamler, Chapel Hill, NC (US); Claude A. Piantadosi, Durham, NC (US); Mark W. Dewhirst, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/986,807

(22) Filed: Nov. 13, 2001

(51) Int. Cl.$^7$ .............................................. A61K 31/535
(52) U.S. Cl. ...................... 514/236.5; 514/18; 514/509; 514/535; 514/611; 514/561; 514/742
(58) Field of Search ............................... 514/6, 18, 509, 514/236.5, 535, 611, 561, 742

(56) References Cited

U.S. PATENT DOCUMENTS

| | | | | |
|---|---|---|---|---|
| 4,900,719 A | * | 2/1990 | Means et al. .................. 514/18 |
| 5,385,940 A | * | 1/1995 | Moskowitz ................. 514/565 |
| 5,731,305 A | * | 3/1998 | Keefer et al. ............... 514/183 |
| 5,861,168 A | * | 1/1999 | Cooke et al. ............... 424/424 |
| 5,873,359 A | * | 2/1999 | Zapol et al. ........... 128/203.12 |
| 6,063,407 A | * | 5/2000 | Zapol et al. ................. 424/718 |
| 6,314,956 B1 | * | 11/2001 | Stamler et al. ......... 128/200.24 |
| 6,337,321 B1 | * | 1/2002 | Cooke et al. .................. 514/44 |
| 6,340,480 B1 | * | 1/2002 | Duckett et al. ............. 424/728 |
| 6,358,536 B1 | * | 3/2002 | Thomas ...................... 424/608 |

OTHER PUBLICATIONS

Bing et al, Biochemical And Biophysical Research Communications, vol. 275, pp. 350–352, 2000.*

* cited by examiner

Primary Examiner—James H. Reamer (57) ABSTRACT

Patients with pathologic conditions involving constriction or proliferation of smooth muscle or disease associated with cysteine containing proteins, or who are at risk for such, are administered a therapeutically effective amount of a nitric oxide (NO) donor which is insufficient to acutely lower mean arterial blood pressure or pulmonary artery pressure by more than 10%. In one subgenus, NO donor is administered to modify red blood cell membrane receptors to prevent red blood cells from causing vasoconstriction. A related method which allows increased dosage of NO donor without acutely lowering mean arterial blood pressure comprises administering the NO donor into an artery of the patient. In another method, patients having a cardiovascular syndrome, or who are at risk for such, are administered a therapeutically effective amount of thiol which does not acutely affect blood pressure to a significant degree.

27 Claims, 5 Drawing Sheets

USE OF THERAPEUTIC DOSAGES FOR NITRIC OXIDE DONORS WHICH DO NOT SIGNIFICANTLY LOWER BLOOD PRESSURE OR PULMONARY ARTERY PRESSURE

TECHNICAL FIELD

One invention relates to prophylaxis or treatment of pathologic conditions involving constriction or proliferation of smooth muscle or of disease associated with cysteine-containing proteins. A different invention relates to prophylaxis or treatment of a patient in need of a nitric oxide donor and increased blood pressure. Still another invention is directed to prophylaxis or treatment of cardiovascular syndromes.

BACKGROUND OF THE INVENTION

Nitric oxide (NO) donors are known to be useful for therapeutic utility, e.g., to prevent restenosis following angioplasty (Groves, P., et al., Cardiovascular Research 26, 615–619 (1992)), to inhibit platelets to prevent coagulation and thrombus formation (Groves, P., et al., Circulation 87, 590–597 (1993)) and to treat angina (Knight, et al., Circulation 95, 125–132 (1997)). NO donors are considered to have additional therapeutic utility in cancer, killing microbes and viruses, relaxing airways and intestinal smooth muscle (e.g., for treating asthma and esophageal spasms), in promoting erectile function and in treatment of heart failure and urinary incontinence. The dosages used and considered to be necessary have, at the very least, the effect of lowering systemic blood pressure and pulmonary artery pressure, by relaxing of smooth muscle, a result which has been viewed as a basis for efficacy. In many cardiovascular syndromes, e.g., myocardial infarction and heart failure, standard therapy involves maximal non-harmful lowering of blood pressure as this lowers stress on the heart.

SUMMARY OF THE INVENTION

It has been discovered herein that NO donors, as defined herein, can block constriction and thus ameliorate (and prophylax against) pathological constriction of smooth muscle at doses below those that relax smooth muscle and can desensitize receptors at doses that have no effect on vascular tone.

One embodiment of an invention herein, denoted the first embodiment, is directed at a method for prophylaxis or treatment of a patient with a pathologic condition involving constriction or proliferation of smooth muscle, e.g., diseases of the vasculature, or who is at risk for such, except for a patient having acute thrombotic complications of restenosis or platelet embolism or other thromboembolic event (e.g., pulmonary embolism or embolic stroke secondary to endocarditis), said method comprising administering an NO donor which is capable of acutely lowering mean arterial blood pressure or pulmonary artery pressure by more than 10% to said patient in a therapeutically effective amount which is insufficient to acutely lower mean arterial blood pressure or pulmonary artery pressure by more than 10%, e.g., by more than 5% (i.e., by amounts that would be otherwise viewed as non-therapeutic). The exception for acute thrombotic complications of restenosis is because Langford, E. J., et al., Lancet 344, 1458–460 (1994) describes low dose administration of NO donor in the setting of putting in a stent and because Kaposzta, Z., et al., Circulation 103, 2371–2375 (2001) shows low dose administration of NO donor decreases platelet embolism and because S-nitrosoglutathione has been shown previously to inhibit other thromboembolic events at doses that do not acutely drop blood pressure reflecting a more potent effect on platelets than on blood pressure. However, there has been no disclosure previously of use of NO donors as defined herein, to treat disorders of blood vessels without acutely dropping blood pressure or directly affecting tone in these vessels, e.g., for treatment of vasospasms or long term antiproliferation or antiatherogenic effect or long term amelioration of systemic hypertension or pulmonary hypertension.

Another embodiment of the invention herein, denoted the second embodiment, is directed to a method for prophylaxis or treatment of a patient with a disease associated with a receptor having a cysteine residue or other cysteine containing protein that is modified by NO donor to alter its function, or at risk therefor, comprising administering an NO donor which is capable of acutely lowering mean arterial blood pressure or pulmonary artery pressure by more than 10% to said patient in a therapeutically effective amount which is insufficient to acutely lower mean arterial blood pressure or pulmonary artery pressure more than 10%, e.g., by more than 5%. The term "disease associated with" is used herein to mean a disease in which over or under activation of the receptor or other protein is implicated in the disease.

The term "acutely lower mean arterial blood pressure or pulmonary artery pressure more than 10%, e.g., by more than 5%," is used herein to mean lowering of mean arterial blood pressure or pulmonary artery pressure more than 10%, e.g., by more than 5%, by a single dose of a drug over the period of the half-life of the drug.

Pulmonary artery pressures are measured in the pulmonary artery according to a standard method using a Swan-Ganz catheter.

The first and second embodiments are directed to prophylaxis or treatment. The treatment can involve patients without symptoms in an inactive state of disease to prevent or delay reoccurrence in response to an aggravating stimulus. For example, in the cases of unstable angina or asthma, a patient may be in an inactive status, but symptoms will recur rapidly in response to aggravating stimulus. Thus treatment can be of the disease where symptoms have already been relieved or reduced but sensitivity to aggravating stimulus persists.

A different invention herein, denoted the third embodiment, is directed to treating a patient in need of an NO donor and increased blood pressure, comprising administering a therapeutically effective amount of NO donor directly into an artery of the patient (in distinction to other routes of administration).

Still another invention herein, denoted the fourth embodiment, is directed to a method for the prophylaxis or treatment of a patient with a cardiovascular syndrome, or at risk therefor, comprising administering a therapeutically effective amount of thiol which is insufficient to acutely lower mean arterial blood pressure or pulmonary artery pressure by more than 10%, e.g., by more than 5%.

Usefulness of the result of not acutely lowering blood pressure in some cases is supported by Bing, R. J., et al., Biochem. Biophys. Res. Com. 275, 350–353 (2000).

DETAILED DESCRIPTION

We turn now to the method of the first embodiment of the invention herein, that is to the method for prophylaxis or treatment of a patient with a pathologic condition involving constriction or proliferation of smooth muscle or who is at risk for such, except for a patient having acute thrombotic complications of restenosis or platelet embolism or other thromboembolic event, said method comprising administering an NO donor which is capable of acutely lowering mean arterial blood pressure or pulmonary artery pressure by more than 10% to said patient in a therapeutically effective amount which is insufficient to acutely lower mean arterial blood pressure or pulmonary artery pressure by more than 10%, e.g., by more than 5%.

The treatment is directed to patients with a pathological condition involving constriction or proliferation of smooth muscle.

The prophylaxis is directed to patients who are at risk for a pathological condition involving constriction or proliferation of smooth muscle.

Pathological conditions involving constriction or proliferation of smooth muscle are, for example, acute coronary spasm (e.g., from angina, myocardial infarction and all ischemic syndromes), pulmonary hypertension (e.g., from heart failure, primary pulmonary hypertension and chronic obstructive pulmonary disease, i.e., COPD), systemic hypertension, asthma, rectal spasm, esophageal spasm, pyloric stenosis, and stroke. Of these, coronary spasm, pulmonary hypertension, systemic hypertension, and heart failure are diseases of vascular smooth muscle. Asthma involves airway smooth muscle. Rectal spasm and esophageal spasm and pyloric stenosis involve gastrointestinal smooth muscle. All these pathological conditions involve constriction of smooth muscle except for heart failure. Pulmonary hypertension, pyloric stenosis and asthma involve proliferation of smooth muscle. In respect to systemic hypertension, the invention causes no acute drop in mean arterial blood pressure but reduction over time (analogous to treatment of depression), e.g., over 2 weeks; this is an important effect in the vast majority of cases of hypertension, where the risk accumulates over many years and acute effects are not relevant.

We turn now to the NO donor which is administered. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFKκB. NO donors including S-nitroso, O-nitroso, C-nitroso and N-nitroso compounds and nitro derivatives thereof and metal NO complexes, but not excluding other NO bioactivity generating compounds, useful herein are described in "Methods in Nitric Oxide Research," edited by Feelisch, M., and Stamler, J. S., John Wiley & Sons, New York, 1996, pages 71–115 which is incorporated herein by reference. NO donors which are C-nitroso compounds where nitroso is attached to a tertiary carbon which are useful herein include those described in U.S. patent application Ser. No. 09/695,934. Examples of S-nitroso compounds including S-nitrosothiols useful herein include, for example, S-nitrosoglutathione, S-nitroso-N-acetylpenicillamine, S-nitroso-cysteine and ethyl ester thereof S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, nitroglycerin, SIN1 which is molsidomine, furoxamines, N-hydroxy (N-nitrosamine) and perfluorocarbons that have been saturated with NO or a hydrophobic NO donor. The NO donors herein are ones that acutely lower blood pressure or pulmonary artery pressure if the dose administered is high enough. A discovery herein is that these same NO donors can still block constriction and thus ameliorate (and prophylax against) pathological constriction of smooth muscle and can desensitize receptors at lower dosages which do not acutely lower blood pressure or pulmonary artery pressure. The term NO donors capable of lowering mean arterial blood pressure or pulmonary artery pressure by more than 10% is used herein to mean NO donor, the administration of which, will lower mean arterial blood pressure or pulmonary artery pressure by more than 10% if the dose administered is high enough, and is used herein to distinguish NO donors, the administration of which will not cause acute lowering of mean arterial blood pressure or pulmonary artery pressure by more than 10% regardless of dosage. It appears that an NO donor which will not acutely lower mean arterial blood pressure by more than 10% regardless of dosage is described in Bing, R. J., et al., Biochem. Biophys. Res. Com. 275, 350–353 (2000) and is referred to therein as 2-hydroxybenzoic acid 3-nitrooxymethylphenyl ester and also as B-NOD; regardless of whether or not B-NOD will acutely lower mean arterial blood pressure or pulmonary artery pressure by more than 10% at some dosage, it is meant to exclude B-NOD from the NO donors herein.

As indicated above, administration is of the NO donor is in a therapeutically effective amount which is insufficient to acutely lower mean arterial blood pressure or pulmonary artery pressure more than 10%, e.g., by more than 5% (and thus previously deemed ineffective). Additionally, the dosage is insufficient to raise FEVI by 10% or more (and thus previously viewed as ineffective) for the treatment or prophylaxis of asthma as measured by standard medical approaches, e.g., spirometry, insufficient to lower gastrointestinal muscle tone by more than 10% in the treatment or prophylaxis of rectal spasm by as measured by standard medical approaches, e.g., manometry, insufficient to lower esophageal smooth muscle tone by more than 10% in the treatment or prophylaxis of esophageal spasm as measured by standard medical approaches, e.g., manometry, and insufficient to dilate the pyloris by more than 10% in the treatment or prophylaxis of pyloric stenosis as measured by standard medical approaches, e.g., manometry.

The therapeutically effective amount is an amount that ameliorates a symptom or symptoms of the condition being treated or in the case of prophylaxis an amount that prevents symptom(s) from occurring or causes the symptom(s) which occur to be less in intensity than those that would occur without the administration of the invention. For acute coronary spasm, symptom(s) that are ameliorated include chest pain, hypoxemia and myocardial infarction or size of infarction is decreased. For pulmonary hypertension, symptom (s) that are ameliorated include heart failure, shortness of breath and cough. For systemic hypertension, symptom(s), signs, that are ameliorated include headache, but need not be present. For asthma, symptom(s) which are ameliorated include shortness of breath, cough and wheezing. For rectal spasm, symptoms that are ameliorated include pain. For esophageal spasm, symptoms that are ameliorated include pain. For pyloric stenosis, symptom(s) which are ameliorated include pain and insufficient food intake. For stroke, symptoms which are ameliorated include cognitive, sensory, and motor symptoms. In all these cases, prophylaxis involves administration to those at risk to prevent the symptoms from occurring or causes the symptom(s) which do occur to be less in intensity than those which would otherwise occur and treatment involves administration to those having the disease or condition even if asymptomatic.

In general, administering a therapeutically effective amount for the first embodiment involves administration in an amount to achieve a concentration of NO donor in the blood of 100 picomolar to 100 micromolar (depending on the drug administered and the disease treated or at risk for) which is less than the amount which acutely lowers mean arterial blood pressure more than 10%, e.g., by more than 5%, for example, less than amounts causing at least 50% smooth muscle relaxation, ie., micromolar amounts, or to achieve concentration less than that which lowers pulmonary artery pressure more than 10%, e.g., by more than 5%. Amounts of drug will vary depending on NO donor as well as disease state.

Routes of administration for the first embodiment for NO donor include, for example, intravenous, nebulized, aerosolized, topical, sublingual, and subcutaneous but not intraarterial. Ethyl nitrite may be administered, for example, as a gas or in an infusion.

We turn now to the method of the second embodiment of the invention herein, that is to the method for prophylaxis or treatment of a patient with a disease associated with a receptor having a cysteine residue or other cysteine containing protein that is modified by NO donor to inhibit or stimulate its function or at risk therefor, comprising administering an NO donor which is capable of acutely lowering mean arterial blood pressure or pulmonary artery pressure by more than 10% to said patient in a therapeutically effective amount which is insufficient to acutely lower mean arterial blood pressure or pulmonary artery pressure by more than 10%, e.g., by more than 5%.

Receptors having cysteine residues include serotonin receptors, adrenergic receptors, NMDA receptors, ryanodine receptors, muscarinic receptors, and kinin receptors. In one subgenus of the second embodiment, the receptors having a cysteine residue also include membrane receptors. In a different subgenus of the second embodiment, the receptors having a cysteine residue do not also include membrane receptors.

Other cysteine containing protein that is modified by NO donor to inhibit its function includes NFκB, AP1, ras, $Na^+$ channels, $Ca^{2+}$ channels, $K^+$ channels, and prion protein. (See Stamler, J. S., Cell, 2001.)

Diseases associated with serotonin receptors treatable in the second embodiment herein include, for example, depression, stress, anxiety and atherosclerosis.

Diseases associated with adrenergic receptors include, for example, systemic hypertension, pulmonary hypertension and coronary artery disease.

Diseases associated with NMDA receptors include, for example, atherosclerosis, neurodegeneration, Alzieimer's disease, dementia, Parkinson's disease, stress and anxiety.

We turn now to the membrane receptors. In one subgenus of the second embodiment, the NO donor is administered to modify membrane receptors, such as those in red blood cells, e.g., AEI protein; this prevents the causing of vasoconstriction by red blood cells and decreases the associated risk of heart attack, stroke, pulmonary hypertension and systemic hypertension and thus mitigates the cardiovascular toxicity associated with red blood cells. The method of this subgenus includes infusing NO donor in an amount which is insufficient to acutely lower mean arterial blood pressure and pulmonary artery pressure more than 10%, e.g., more than 5%, but which is a therapeutic amount to load red blood cells to prevent vasoconstricting effect of red blood cells and prophylax against or treat ischemic disorders, sickle cell disease, and thalassemias.

We turn now to the cysteine containing proteins that are not receptors.

Diseases that are associated with NFκB, $Ca^{2+}$ and $K^+$ channels include stroke and heart failure.

Diseases that are associated with other cysteine containing protein that is not receptor include prion related diseases, e.g., Creutzfeldt-Jacob disease, kuru and mad cow disease, and malignant hyperthermia.

We turn now to the method of the second embodiment generally.

The treatment involves administration to those having the disease.

The prophylaxis involves administration to those at risk for the disease.

The NO donors administered are the same as in the case of the first embodiment.

We turn now to the amount of NO donor administered in the second embodiment. As indicated above, this is a therapeutically effective amount of NO donor which is insufficient to acutely lower mean arterial blood pressure or pulmonary artery pressure more than 10%, e.g., by more than 5%, and which changes blood vessel diameter less than 10%.

The therapeutically effective amount for the second embodiment is an amount that ameliorates a symptom or symptoms of the disease being treated or in the case of prophylaxis an amount that prevents symptoms from occurring or causes the symptom(s) which occur to be less in intensity than those which would occur without the administration of the invention. For treatment or prophylaxis of depression, the amount is an amount effective to ameliorate the presence or occurrence of symptoms of depression, e.g., morbid mood, sleep disorder and inability to experience grief, joy or pleasure. For treatment or prophylaxis of stress, the amount is an amount effective to ameliorate the presence or occurrence of fear and anxiety. For treatment or prophylaxis of anxiety, the amount is an amount effective to ameliorate the presence or occurrence of symptoms of restlessness, unusual fatigability, difficulty in concentration, irritability, muscle tension and disturbed sleep. For treatment or prophylaxis of atherosclerosis, the amount is an amount effective to ameliorate the presence or occurrence of symptoms of vasospasm, ischemia, myocardial infarction, progression of atherosclerotic lesions and heart failure. For prophylaxis of systemic hypertension, the amount is an amount effective to control blood pressure to improve symptoms, e.g., headache, and to prevent stroke or other complication. In the treatment or prophylaxis of pulmonary hypertension, the amount is an amount effective to ameliorate the presence or occurrence of symptoms as described above. In the treatment or prophylaxis of heart failure, the amount is an amount effective to ameliorate the presence or occurrence of symptoms of shortness of breath, fatigue, exercise intolerance, and swelling of the legs. In the treatment or prophylaxis of asthma or COPD, the amount is an amount effective to ameliorate the presence or occurrence of symptoms as described above. In the treatment or prophylaxis of neurodegeneration, the amount is an amount effective to ameliorate the presence or occurrence of symptoms of cognitive, motor, sensory, and vestibular impairment. In the treatment or prophylaxis of Alzheimer's disease, the amount is an amount effective to ameliorate the presence or occurrence of symptoms of memory loss or other impairments as recited in standard textbooks. In the treatment or prophylaxis of dementia, the amount is an amount effective to ameliorate the presence or occurrence of cognitive symptoms or other related impairments as defined in standard textbooks. In the treatment or prophylaxis of a prion-related disease, the amount is an amount effective to ameliorate the presence or occurrence of cognitive symptoms or psychological impairment. In the treatment or prophylaxis of coronary artery disease, the amount is an amount effective to ameliorate the presence or occurrence of symptoms of pain or myocardial infarction or to decrease its size. In a treatment or prophylaxis involving red blood cells, the amount is an amount effective to prevent vasoconstricting effect of red blood cells.

Benefit is obtained because the doses used herein are sufficient to desensitize receptors and alter other proteins involved in disease where hyposensitivity mediates or potentiates the occurrence and intensity of symptoms. For example, for prophylaxis or treatment of atherosclerosis, the administration of the second embodiment negates sensitivity to vasospasm, ischemic and myocardial infarction. Benefit is obtained because dosages functional to desensitize receptors and other disease involved proteins include dosages which have no effect on vascular tone. The goal here is to mitigate hyposensitivity without affecting vascular tone or blood pressure. The dosages used for the second embodiment are those that mitigate hyposensitivity without affecting vascular tone.

In general, administering a therapeutically effective amount for the second embodiment involves administration to provide in blood a concentration of NO donor of 100 picomolar to 100 micromolar (depending on the drug administered and the disease treated or at risk for) which is less than the amount which acutely lowers the mean arterial blood pressure or pulmonary artery pressure more than 10%, for example, more than 5%, for example, less than micromolar amounts, or equivalent amount of NO bioactivity.

Routes of administration for the second embodiment herein, include, for example, intravenous, oral, subcutaneous, nebulized, bur not intraarterial.

We turn now to the third embodiment herein, i.e., the method herein for treating a patient in need of an NO donor and of increased blood pressure, comprising administering a therapeutically effective amount of NO donor directly into an artery of the patient.

The patients for this method include, for example, those having the disorders of sepsis or orthostatic hypotension or hypotention of any cause with mean arterial blood pressures less than 90 mm Hg or systolic blood pressure less than 90 mm Hg.

The NO donors are those described above and include, for example, S-nitrosohemoglobin and S-nitrosoglutathione.

The therapeutically effective amount is an amount which relieves symptoms of the disorder being treated and raises mean arterial blood pressure by at least about 10%, e.g., from 90 to 100 mm Hg. The amounts depend on the drug being administered but generally provide nanomolar to micromolar concentrations of drug in the blood.

This method is related to the first and second embodiments described above in allowing increased dosage compared to what is described for the first and second embodiments without acutely lowering mean arterial blood pressure.

We turn now to the fourth embodiment herein, i.e., the method herein for the prophylaxis or treatment of a patient with a cardiovascular syndrome, or at risk therefor, comprising administering a therapeutically effective amount of a thiol which is insufficient to acutely lower mean arterial blood pressure or pulmonary artery pressure by more than 10%, e.g., by more than 5%.

The term "cardiovascular syndrome" is used herein to mean heart disease, stroke, transient ischemic attack, ischemic coronary syndrome, peripheral vascular disease, claudication, impotence, and mesenteric or other organ ischemia.

The treatment is directed to patients with a cardiovascular syndrome.

The prophylaxis is directed to patients at risk for a cardiovascular syndrome.

The thiols useful in the fourth embodiment are those that, when added to blood, promote S-nitrosothiol formation in blood, i.e., cause increase in levels of circulating endogenous S-nitrosothiols. The term "circulating" is used to mean circulating in blood. Addition of thiol to blood to raise circulating endogenous S-nitrosothiol levels is described in Lipton, Nature, 2001.

Suitable thiols for use in the fourth embodiment include, for example, glutathione and N-acetylcysteine.

The therapeutically effective for the fourth embodiment is an amount that causes increase in level of circulating S-nitrosothiols and thereby ameliorates a symptom or symptoms of the pathological condition being treated, or in the case of prophylaxis prevents symptoms from occurring or causes the symptom(s) which occur to be less in intensity than those that would occur without the administration of the invention. For the treatment of angina, for example, the therapeutically effective amount is an angina ameliorating amount. Increase in level of circulating S-nitrosothiols can be measured as described in Feelisch, M. and Stamler, J. S., "Methods in Nitric Oxide Research," John Wiley & Sons, New York, 1996.

In general, administering a therapeutically effective amount for the fourth embodiment involves administration to provide in the blood a concentration of administered thiol of 1 nanomolar to 10 millimolar (depending on the drug administered and the disease treated, or at risk for) which is less than the amount which acutely lowers the mean arterial blood pressure and pulmonary artery pressure by more than 10%, e.g., by more than 5%.

Routes of administration for the second embodiment, include, for example, oral and intravenous administration.

Thus, in the fourth embodiment herein, thiol, e.g., glutathione or N-acetylcysteine, is given to a patient, e.g., by oral or intravenous administration, at concentrations that do not acutely change blood pressure or pulmonary artery pressure, in order to raise the circulating levels of endogenous S-nitrosothiols. Lipton (Nature, 2001) has shown that thiol added to blood promotes S-nitrosothiol formation. The fourth embodiment herein differs from Lipton in administering amounts of thiol that do not acutely affected mean arterial blood pressure or pulmonary artery pressure in a significant degree.

The following working examples, show scientific basis for the invention or are directed to treatment or prophylaxis according to the inventions herein.

EXAMPLE I

Avascular ring bioassay is carried out on mouse aorta rings as described in Stamler, J. S., PNAS 89, 8087–8091 (1992). The assay involves a chamber of solution into which mouse aorta ring attached to a force transducer is placed where the solution is bubbled with 21% $O_2$/5% $CO_2$/balance $N_2$. The force transducer moves a pen in response to contraction and relaxation effects to give a tracing of forces (tension) in the Y-direction versus time in the X-direction on a chart.

Various agents as described later are applied to the aorta rings to give to give contraction and relaxation effects. Tracings of force (tension) in the Y-direction versus time in the X-direction are obtained with upward direction indicating contraction and downward direction indicating relaxation.

Figure 1:
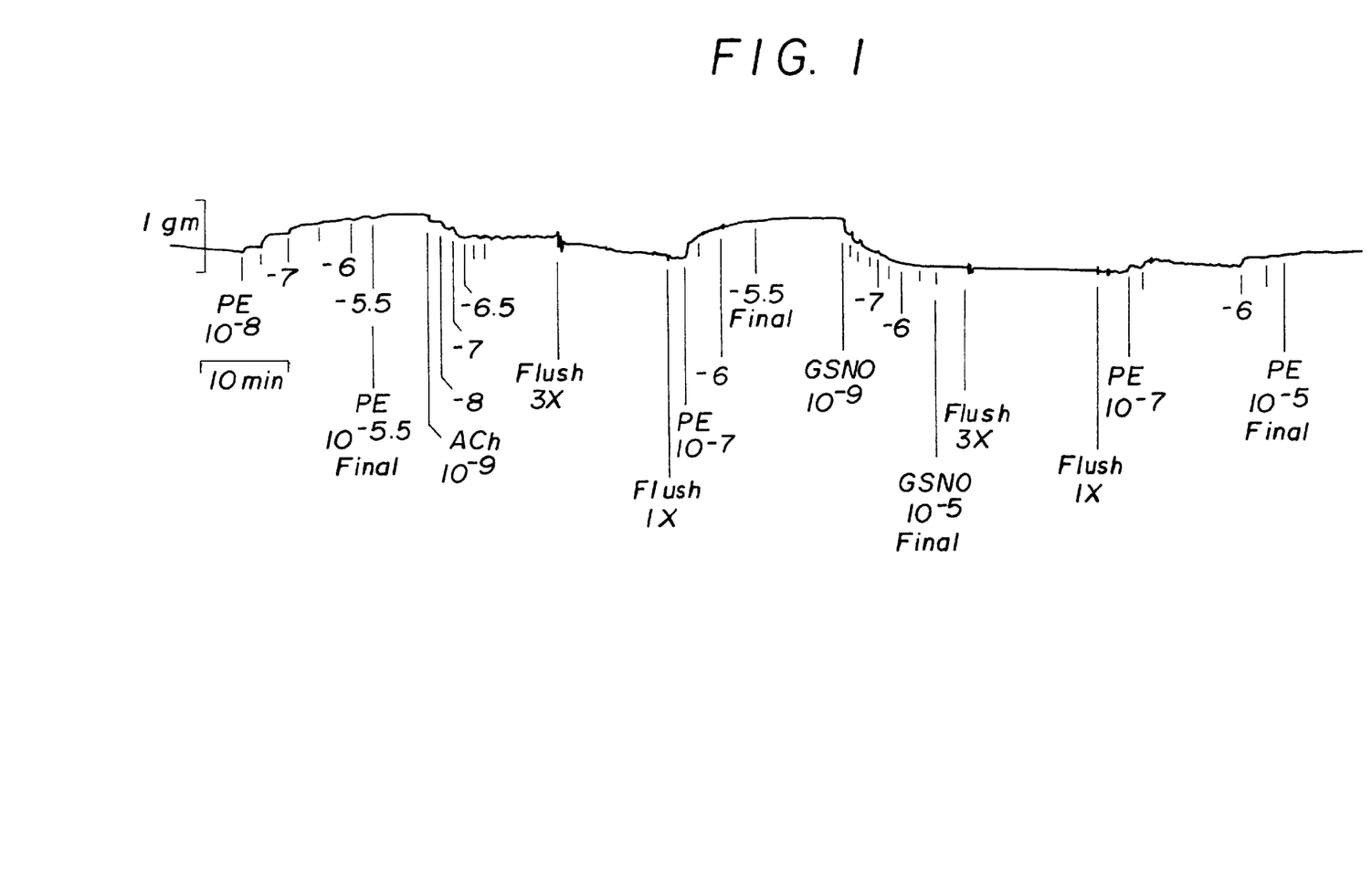
FIG. 1 is a tracing of tension (force) versus time with respect to in vitro testing on a mouse aorta with concentration of added compounds shown along the tracing and shows results of Example I of blocking constriction responses to agonists at concentrations of NO donor which would not significantly lower blood pressure and do not directly increase the tone of the vessel.

Experimental conditions and results (the tracing) are shown in FIG. 1. As shown in FIG. 1, there is a 1 gram contraction range; this means 1 gram of tension is applied. The distance in the X-direction representing 10 minutes is shown on FIG. 1 at the left. On FIG. 1, "E" means application of phenylephrine, a constricting agent, and the concentrations thereof at particular times are denoted; "ACh" means application of acetylcholine (which causes a relaxation effect in response to endogenous nitric oxide) and the concentration thereof at particular times are denoted; and "GSNO" means application of S-nitrosoglutathione, an NO donor, and the concentrations thereof at particular times are denoted.

As shown in FIG. 1, phenylepirine is applied starting at time zero at a concentration of $10^{-8}$ molar increasing to a concentration of $10^{-5.5}$ molar, and this causes a contracting effect. As further shown in FIG. 1, acetylcholine is then applied at a concentration of $10^{-9}$ molar increasing to a concentration of $10^{-6.5}$ and causes a relaxing response as a result of causing production of endogenous NO. As further shown in FIG. 1, flushing is then carried out three times then and one more time; the flushing is carried out (with Krebs-Henseleit solution described hereinafter in Example III) and removes the acetylcholine. As further shown in FIG. 1, phenylephrine is then applied starting at a concentration of $10^{-7}$ molar increasing to a concentration of $10^{-5.5}$ molar. This causes a contracting response despite the previous application of acetylcholine. As further shown in FIG. 1, S-nitrosoglutathione is then applied starting at a concentration of 1 nanomolar, increasing to a concentration of 10 micromolar, and this causes a relaxing (contraction-attenuating) effect. As further shown in FIG. 1, flushing is then carried out three times (with Krebs-Henseleit solution); and then one more time with the same flushing agent; this flushing removes the S-nitrosoglutathione. As further shown in FIG. 1, phenylephrine is then applied at a concentration of $10^{-7}$ molar, increasing to $10^{-5}$ molar; this does not cause a contracting response.

The experiment shows that unlike endogenous NO, the application of NO donor modifies adrenergic receptor and prevents adrenergic agonist (phenylephrine) from working and that pretreatment with NO donor blocks subsequent response to adrenergic agonist.

EXAMPLE II

A vascular ring bioassay was carried out as follows: Artery rings (3 mm) were harvested from New Zealand white rabbits and mounted in 25 ml tissue baths filled with Krebs-Henseleit buffer and bubbled with 21% $O_2$/5% $CO_2$/balance $N_2$. Isometric tension was measured. All rings in the study were suspended with similar baseline levels of tension (~2 g). Tissue baths were thoroughly rinsed with fresh buffer between interventions.

Three runs were carried out. In one run denoted the control, no additive was added. In a second run, S-nitrosoglutathione (GSNO) was added to provide a concentration of 1 $\mu$M (which has no effect on resting tone but which as shown later prevents contraction). In a third run, SIN1 was added to provide a concentration of 1 $\mu$M. The NO donors did not cause a relaxing effect at the concentrations used.

After flushing with solution as described in Example I, phenylephrine was then added in each case to provide a concentration of 1 to 10 $\mu$M.

Figure 2:
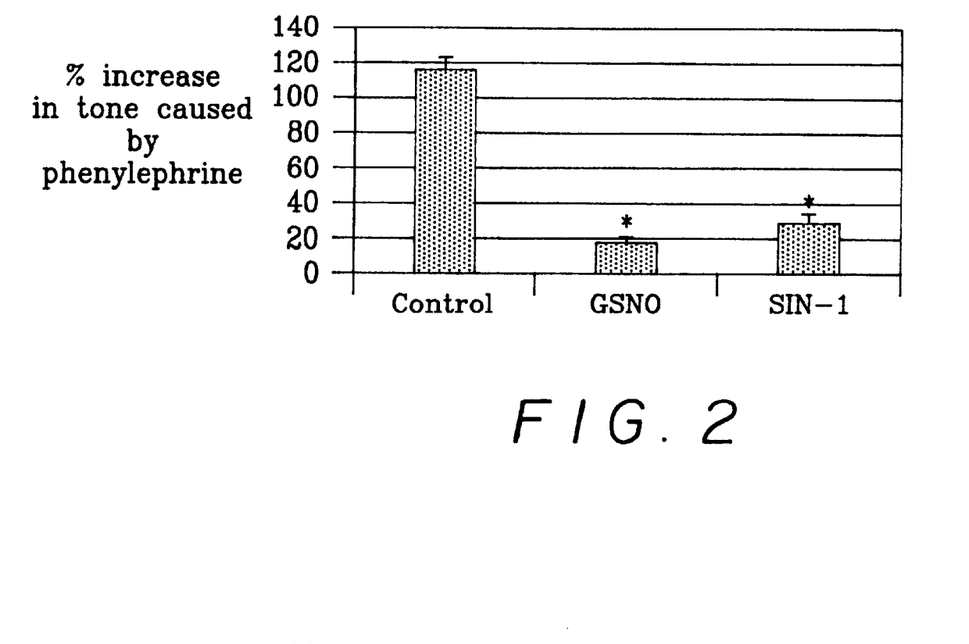
FIG. 2 depicts bar graphs of increase in constricting effect cause by phenylephrine ($10^{-6}$ M) in an in vitro arterial ring bioassay for control and following exposure to amounts of NO donors that have no effect on vascular tone directly but which block the constriction and shows results of Example II.

The results are shown in FIG. 2 where percent increase in tone is indicated on the Y-axis and additive or absence thereof (control) is indicated on the X-axis.

As shown in FIG. 2, there was over a 100% increase in tone for the control case and less than 30% increase in tone in the cases of GSNO and SIN1 indicating the NO donors used at levels that had no effect on vascular resting tone blocked constriction responses to adrenergic agonist (phenylephrine). Thus the NO donors at concentrations not affecting baseline tone mitigated subsequently imparted constricting impetus but did not relax the blood vessels.

EXAMPLE III

The experiments of this example were performed in isolated buffer-perfused lungs (IPL) of rabbits as described in Nozik-Grayck, E., et al., American Journal of Physiology 273, C296–C304 (1997). The buffer was Krebs-Henseleit (KH) solution containing sodium chloride (82.8 mM), potassium chloride (4.7 mM), monobasic potassium phosphate (2.4 mM), sodium bicarbonate (25 mM), magnesium sulfate (1.2 mM), calcium chloride (2.7 mM), and dextrose (11.1 mM) at pH 7.4. New Zealand white rabbits (May's Farm, NC) weighing 2.5–3.5 kg were anticoagulated with 5,000 U sodium heparin and anesthetized with 25 mg/kg sodium pentobarbital by ear vein. An incision was made in the left chest wall, exposing the heart. The animal was exsanguinated via the left ventricle and the thorax entered by excising the rib cage. Stainless steel cannulas were placed in the trachea, main pulmonary artery and left atrium to measure tracheal (airway) and pulmonary artery pressure. The aorta also was tied with the pulmonary artery to prevent loss of perfusate to systemic circulation. The lungs were inflated with 80 ml of air and ventilated with 21% $O_2$ and 5% $CO_2$ (balance $N_2$) with an animal respirator (Harvard Apparatus Company, Inc., S Natick, Mass.) at a rate of 30 breaths/minute. The tidal volume was adjusted to maintain a peak tracheal pressure of 8–10 torr with a positive end expiratory pressure of 2–3 torr. The perfusion circuit contained a reservoir suspended freely from a force transducer (Model FT100, Grass Instrument Company, Quincy, Mass.) and a water heater set at 37° C. Perfusate was circulated by a roller pump (Sams, Inc., Ann Arbor, Mich.) and passed through a bubble trap before entering the pulmonary artery. The perfusate returned to the left atrium and then to the reservoir which was set at the lowest portion of the lung to provide a left atrial pressure of zero. Perfusion began slowly and was gradually increased to 100 ml/min. After rinsing the lungs free of blood with 500 ml buffer, a recirculating system was established. The total volume in the circuit was approximately 250 ml. Mean pulmonary artery pressure (Ppa) was measured using pressure transducers (P231D, Gould Statham Instruments, Inc., Hato Ray, PR).

Three runs were carried out. In one case (control), no additive was injected into the recirculating system. In a second case, S-nitrosoglutathione (GSNO), 50 µM, was injected into the recirculating system to provide a concentration of nanomolar to micromolar GSNO therein. In a third case, SIN1, 100 µM, was injected into the recirculating system to provide a concentration of nanomolar to micromolar SIN1 therein. The injection of the GSNO (50 µM) and SIN1 (100 µM) did not cause change in Ppa.

Sixty minutes later, the serotoninergic agonist serotonin was injected into the recirculating system in each of the three cases to provide a concentration of 1 micromolar.

Figure 3:
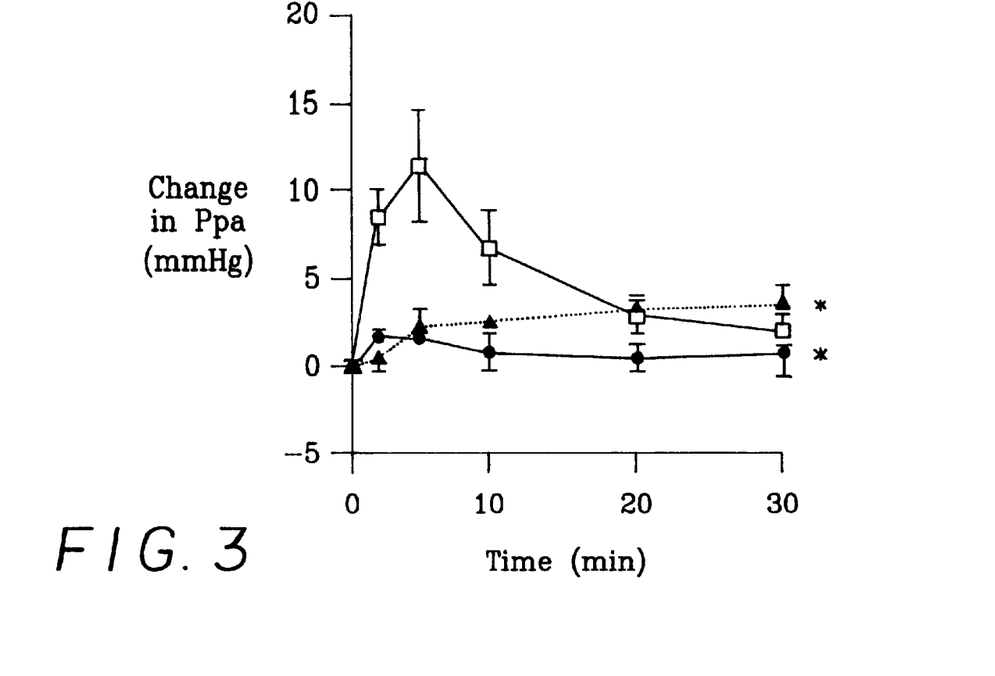
FIG. 3 depicts a graph of time versus change in pulmonary artery pressure in an in vivo isolated-perfused rabbit lung test for control and following pretreatment with NO donors, showing blocking of constricting effect (because Ppa is shown not to go down on pretreatment with NO donor) of serotonin at concentrations of NO donors which have no effect on, i.e., do not lower, pulmonary pressures or decrease pulmonary vascular tone, and shows results of Example III.

The results are shown in FIG. 3 where the filled in circles represent the run with GSNO, the filled in triangles represent the run with SIN1, and the open squares represent control. The Y-axis represents change in Ppa from baseline (baseline is before NO donors were added). As indicated in FIG. 3, both NO donors prevented constriction by agonist (serotonin) which has been implicated in pulmonary vasoconstriction and ischemic syndromes.

In addition, tracheal pressure (airway pressure) measured using pressure transducers, was not altered by the NO donors.

EXAMPLE IV

Figure 4A:
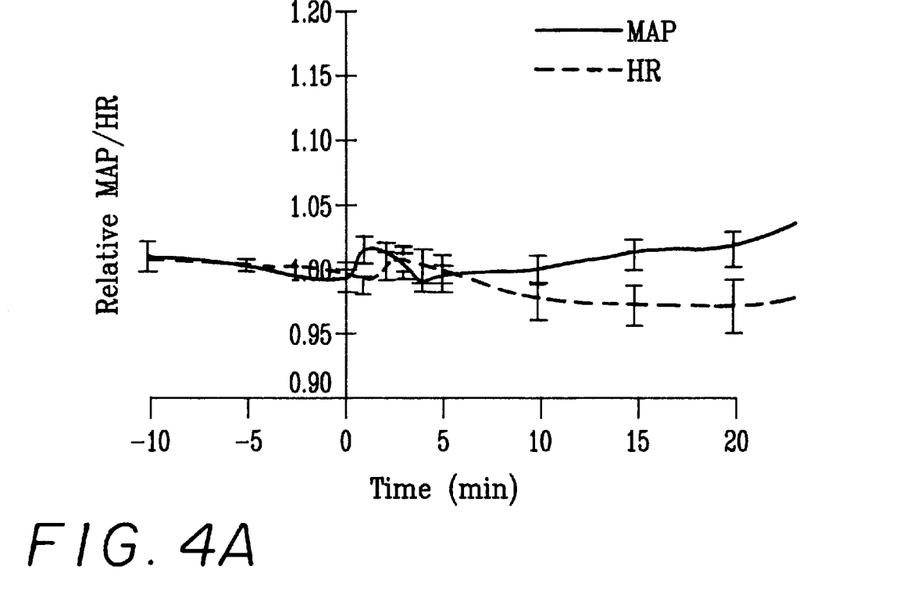
FIG. 4A is a graph of time versus relative mean arterial blood pressure and relative heart rate for intravenous infusion of S-nitrosothiol (S-nitrosohemoglobin) and shows results of Example IV. The time t=0 is the time at which infusion is started.

Rats (n=4) were infused via femoral vein with 200 nmol/kg of S-nitrosothiol (S-nitrosohemoglobin). Mean arterial blood pressure (MAP) and heart rate (HR) were measured. Results are shown in FIG. 4A. As shown in FIG. 4A, the intravenous infusion had no effect on resting blood pressure or heart rate higher doses of S-nitrosothiol cause blood pressure to fall.

Figure 4B:
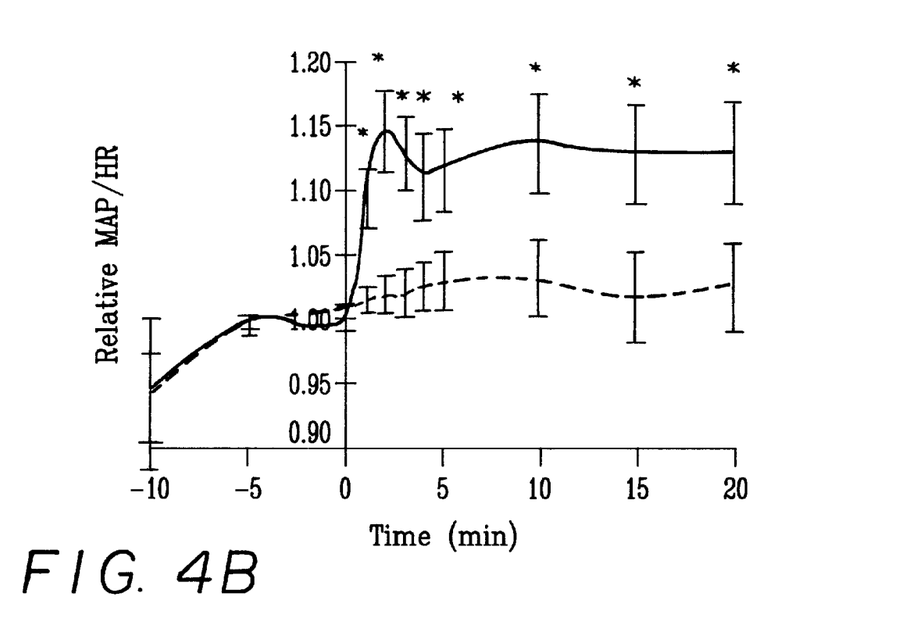
FIG. 4B is a graph of time versus relative mean arterial blood pressure and relative heart rate for intraarterial infusion of S-nitrosothiol (S-nitrosohemoglobin) and shows results of Example IV. Asterisks mean p<0.05 compared to baseline. The time t=0 is the time at which infusion is initiated.

In another case, rats (n=4) were infused via femoral artery with 200 nmol/kg of S-nitrosothiol (S-nitrosohemoglobin). Mean arterial blood pressure (MAP) and heart rate (HR) were measured. Results are shown in FIG. 4B. As shown in FIG. 4B, the intraarterial infusion increased mean arterial blood pressure and heart rate.

In FIG. 4A and FIG. 4B, the continuous lines represent mean arterial blood pressure (MAP) and the lines composed of dashes represent heart rate (HR).

EXAMPLE V

Figure 5:
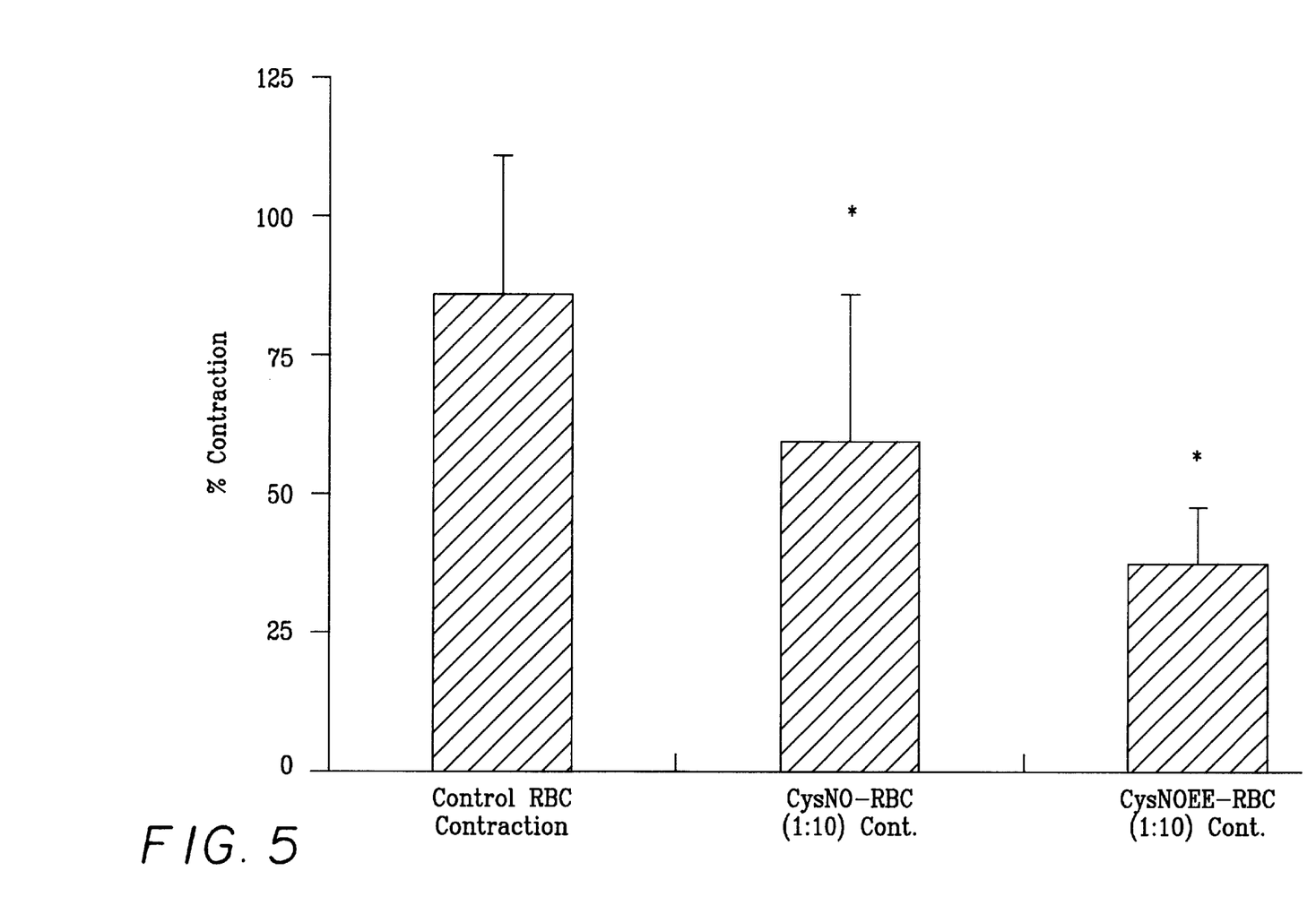
FIG. 5 depicts bar graphs for control, treatment with S-nitrosocysteine and treatment with S-nitrosocysteine ethyl ester, followed by washing free of S-nitrosothiol, showing percent contraction in a rabbit aortic ring bioassay, and shows results of Example V.

Red blood cells (RBC) are treated for 5 minutes with S-nitrosocysteine or S-nitrosocysteine ethyl ester (1:10 ratio of NO to hemoglobin) to load the red blood cells with S-nitrosocysteine or S-nitrosocysteine ethyl ester to nitrosylate membrane receptors including AEI proteins (Pawloski, Nature, 2001) and then washed free of S-nitrosothiol. The nitrosothiol loaded red blood cells and control red blood cells were incubated in a rabbit aortic ring bioassay (described in the first paragraph of Example II). Results are shown in FIG. 5. As shown in FIG. 5, control red blood cells produce contraction of blood vessels. The amount of contraction is above that produced by $10^{-6}$M phenylephrine. As shown in FIG. 5, where S-nitrosocysteine treated red blood cells are denoted CysNO-RBC and S-nitrosocysteine ethyl ester treated red blood cells are denoted CysNOEE-RBC, this contraction is attenuated by S-nitrosylation of receptors. The S-nitrosothiol treatment does not produce relaxation of blood vessels. Similar results are seen if the nitrosothiols are co-incubated in the bioassays with the red blood cells.

EXAMPLE VI

Figure 6A:
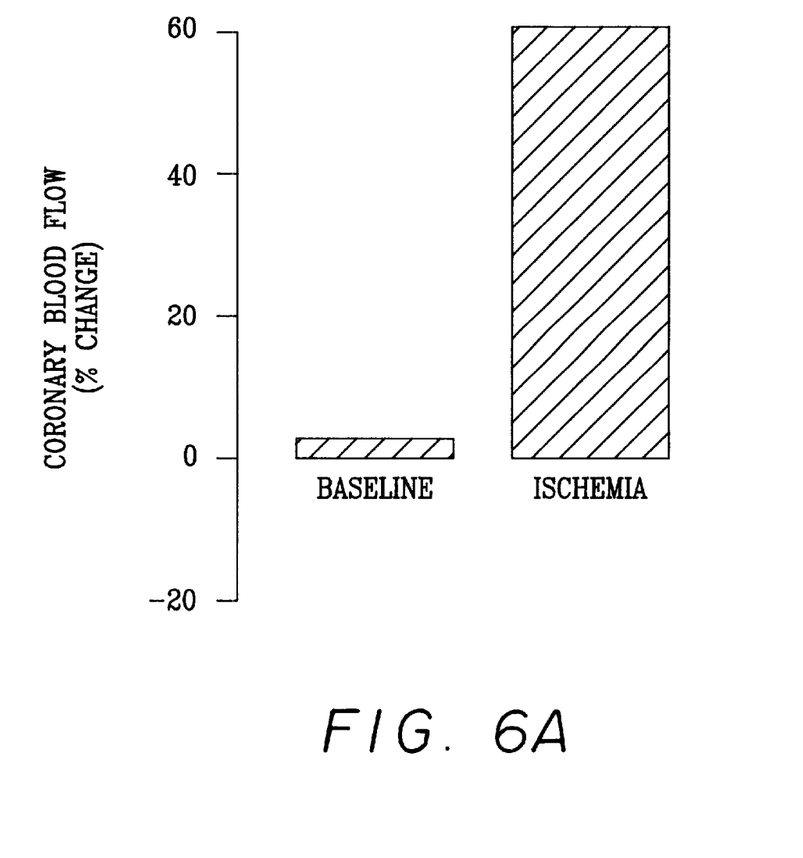
FIG. 6A depicts the effect of red blood cells previously exposed to S-nitrosocysteine on infusion into dogs on coronary blood flow without induction of ischemia and with induction of ischemia, and shows results of Example VI.

Red blood cells previously exposed to S-nitrosocysteine (at ratio of 1:1,000 to 1:10 NO to hemoglobin) to nitrosylate membrane receptors have no effect on coronary blood flow in dogs (see "BASELINE" bar graph in FIG. 6A) but improve coronary flow when ischemia is induced in the dogs (see "ISCHEMIA" bar graph in FIG. 6A). The membrane receptor nitrosylated red blood cells have no effect on blood pressure.

Figure 6B:
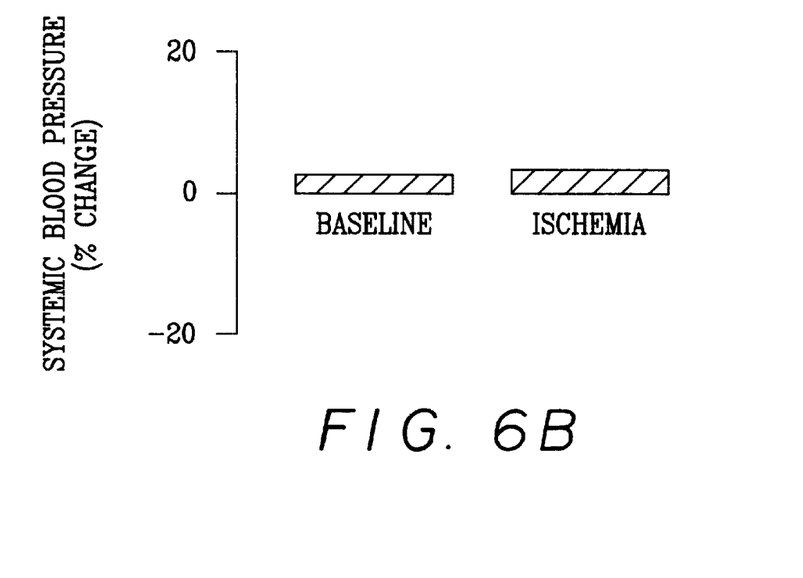
FIG. 6B depicts the effect of infusion into dogs of S-nitrosocysteine or S-nitrosoalbumin on systemic blood pressure without and with induction of ischemia and shows results of Example VI.

In another case, S-nitrosocysteine (3 nmol/kg) or S-nitrosoalbumin (10 nmol/kg) is infused systemically into dogs. Responses are shown in FIG. 6B. As shown in FIG. 6B, the infision of S-nitrosocysteine has no effect on systemic blood pressure even when the dogs are made ischemic. The response to S-nitrosoalbimim infusion is no different. The infusions of NO donors result in reaction with membrane receptors in red blood cells. As shown in FIG. 6A, the reactions with membrane receptors in red blood cells can increase coronary flow in ischemic but not healthy (normotoxic) animals.

EXAMPLE VII

A 70-year-old male who complains of recurrent episodes of acute vasospastic angina is treated with S-nitrosoglutathione (GSNO) at 1–1,000 µg orally 4x/day. Blood pressure is unchanged and acute symptoms resolve. In addition, the frequency of vasospastic chest pain decreases over the following three weeks.

EXAMPLE VIII

A 27-year-old white fermale with primary pulmonary hypertension class II presents complaining of shortness of breath. She is given 10 mM GSNO in 1 cc saline nebulized 3×/day. Symptoms of shortness of breath resolve but pulmonary artery pressure and systemic pressure are unchanged with acute administration. After four months of therapy, pulmonary artery pressure has dropped by 5 mm of mercury and the patient's symptoms have improved. The patient is subsequently given oral GSNO at 10 μg TID and doses are empirically changed to prevent any significant change in blood pressure.

EXAMPLE IX

A 25-year-old white female with poorly controlled asthma presents with an exacerbation. She is treated with inhaled S-nitrosocysteine ethyl ester 1–1,000 μg nebulized in 10 cc which does not significantly improve airway tone. However, the acute episode of asthma is brought under control over the following three days and the patient is subsequently continued on oral GSNO 10 μg Q 6 hours. The frequency of asthma exacerbations decline.

EXAMPLE X

A 60-year-old white male with recurrent rectal spasm is given oral ethyl nitrite 0.125% in ethanol (1 cc) 3×/day. Blood pressure does not change but the symptoms of rectal pain resolve. He then continued on this therapy with a decrease in incidence of rectal pain.

EXAMPLE XI

A 65-year-old alcoholic with esophageal spasm is given 2 cc of 0.125% ethyl nitrite in ethanol 3×/day. Symptoms of esophageal pain resolve and symptoms do not recur on the same maintenance dose.

EXAMPLE XII

An infant with pyloric stenosis is given 2 cc of 0.125% ethyl nitrite in ethanol 3×/day.

Symptoms of intestinal pain resolve.

EXAMPLE XIII

A 65-year-old male presents with a transient ischemic attack evidenced by confusion and headache. Carotid dopplers show 98% new occlusion of the right carotid artery. Systolic blood pressure is 180 mm of mercury. He is given an infusion intravenously of S-nitrosocysteinyl glycine 10 μg with resolution of the headache. The systemic blood pressure remains 175 mm of mercury. Symptoms of headache and confusion resolve. The patient is then maintained on oral S-nitrosoglutathione 1–10 μg 3×/day with no recurrence of transient ischemic symptoms.

EXAMPLE XIV

A 50-year-old black female presents with symptoms of depression. She is begun on oral molsidomine (SIN-1) 10 μg per kg dose-adjusted so that blood pressure is unchanged. Over the following three weeks the symptoms of depression resolve and the patient is maintained on this dose with no recurrence.

EXAMPLE XV

A 40-year-old white male with risk factors of hypertension, diabetes, and hypercholestolemia and a strong family history of atherosclerosis presents with claudication and a leg ulcer. He is begun on an infusion of (SIN-1) 0.3 μm/kg per hour for a total of 1 mg with no change in blood pressure. Symptoms of rest pain resolve. He is then begun on oral S-nitrosoglutathione 1–10 μg 3×/day with improvement of duration of exercise and no recurrence of rest pain.

EXAMPLE XVI

A 60-year-old white male with uncontrolled hypertension of 200/90 mm of mercury on a complex medical regimen including angiotension converting enzyme inhibitor, an alpha blocker, and beta blocker has a blood pressure of 200/110. He is begun on oral GSNO at 1 to 10 micrograms QID and ethyl nitrite 0.025% (1 cc) 3×/day. The blood pressure does not change. However, over the following two weeks the blood pressure falls to 170/100 consistent with better management of his disease. He is maintained on these doses with no further exacerbation.

EXAMPLE XVII

A 56-year-old with hyperhomocystenemia and strong family history of premature coronary artery disease undergoes cardiac cauterization which shows severe three vessel disease. He is begun on oral GSNO titrated so that his resting systolic blood pressure of 100 mm of mercury does not change. He does well with no symptoms of coronary disease over the following three years.

EXAMPLE XVIII

A 68-year-old female complains of anxiety and stress and is begun on nitroglycerin, ½ to 1 inch patch 3×/day titrated to avoid a change in blood pressure or headache, and symptoms are alleviated in 4 days.

EXAMPLE XIX

A 70-year-old white male with congestive heart failure develops hypotension and angina. S-nitrosoglutathione (200 nmol/kg) is infused via the brachial artery over 3 minutes. The angina resolves. The systolic blood pressure rises from 85 mm Hg to 100 mm Hg.

EXAMPLE XX

A 65-year-old white male receiving erythropoietin to raise red blood count depleted because of treatment for cancer or renal failure, develops chest pain (caused by increased concentration of red blood cells). An infusion of S-nitrosocysteine ethyl ester (1–10 nmolkg/min) is given, alleviating chest pain without a change in blood pressure.

EXAMPLE XXI

A 65-year-old white male receiving erythropoietin to raise red blood count depleted by renal failure, develops chest pain (caused by increased concentration of red blood cells). An infusion of N-acetylcysteine (50 ng/kg) is begun, alleviating his chest pain without a change in blood pressure. The patient is then begun on N-acetylcysteine, 600 ng, PO, TID, and frequency of angina decreases and blood pressure drops over three weeks.

VARIATIONS

Many variations will be obvious to those skilled in the art. Therefore, the invention is defined by the claims.

What is claimed is:

1. A method for prophylaxis or treatment of a patient with a disease of the vasculature involving constriction or proliferation of smooth muscle or other pathologic condition involving constriction or proliferation of smooth muscle, or at risk for such, except for acute thrombotic complications of restenosis or platelet embolism or other thromboembolic events, said method comprising administering to said patient an NO donor that donates nitric oxide or a related redox species and provides bioactivity that is identified with nitric oxide and which is capable of acutely lowering mean arterial blood pressure or pulmonary artery pressure by more than 10% in a therapeutically effective amount which is insufficient to acutely lower mean arterial blood pressure or pulmonary artery pressure by more than 10%, with the proviso that when the NO donor is ethyl nitrite, it is administered in a liquid, orally or by infusion.

2. The method of claim 1 where the disease or condition is selected from the group consisting of acute coronary spasm, angina, and pulmonary hypertension.

3. The method of claim 1 where the disease or condition is asthmas or COPD and the dose for the NO donor is insufficient to raise FEV1 by 10% or more.

4. The method of claim 1 where the disease or condition is rectal spasm and the dose for the NO donor is insufficient to lower gastrointestinal muscle tone by more than 10%.

5. The method of claim 1 where the disease or condition is esophageal spasm and the dose for the NO donor is insufficient to lower esophageal muscle tone by more than 10%.

6. The method of claim 1 where the disease or condition is pyloric stenosis and the dose for the NO donor is insufficient to dilate the pyloris by more than 10%.

7. The method of claim 1 where the disease or condition is stroke.

8. The method of claim 1 wherein the disease or condition is systemic hypertension.

9. The method of claim 1 where the administration is given prophylactically to a patient at risk for pathologic condition involving constriction or proliferation of smooth muscle.

10. A method for prophylaxis or treatment of a patient with a disease associated with a receptor having a cysteine residue or other cysteine containing protein that is modified by NO donor to inhibit its function, or at risk therefor, comprising administering to said patient an NO donor that donates nitric oxide or a related redox species and provides bioactivity that is identified with nitric oxide and which is capable of acutely lowering mean arterial blood pressure or pulmonary artery pressure by more than 10% in a therapeutically effective amount which is insufficient to acutely lower mean arterial blood pressure or pulmonary artery pressure more than 10%, with the proviso that when the NO donor is ethyl nitrite, it is administered in a liquid, orally or by infusion.

11. The method of claim 10 where the receptor is a serotonin receptor.

12. The method of claim 11 where the disease is depression.

13. The method of claim 11 where the disease is stress and/or anxiety.

14. The method of claim 11 where the disease is atherosclerosis.

15. The method of claim 10 where the receptor is an adrenergic receptor.

16. The method of claim 15 where the disease is systemic or pulmonary hypertension.

17. The method of claim 15 where the disease is coronary artery disease.

18. The method of claim 10 where the-receptor is a red blood cell membrane receptor.

19. The method of claim 18 where the NO donor is administered in an amount to S-nitrosylate membrane receptors in red blood cells.

20. The method of claim 19 where the NO donor administration is to prevent red blood cells causing vasoconstriction and decrease the associated risk of heart attack, stroke, pulmonary hypertension and systemic hypertension.

21. The method of claim 18 where the NO donor is administered to prophylax against or treat an ischemic disorder, sickle cell disease or a thalassemia.

22. A method for treating a patient in need of an NO donor and increased blood pressure comprising administering a therapeutically effective amount of NO donor directly into an artery of the patient.

23. A method for the prophylaxis or treatment of a patient with a cardiovascular syndrome, or at risk therefor, comprising administering a therapeutically effective amount of a thiol which is insufficient to acutely lower mean arterial blood pressure or pulmonary artery pressure more than 10%.

24. The method of claim 1 where the NO donor is an S-nitroso compound.

25. The method of claim 1 where the NO donor is ethyl nitrite in a liquid.

26. The method of claim 10 where the NO donor is selected from the group consisting of S-nitroso compounds, nitroglycerin and molsidomine.

27. The method of claim 10 where the NO donor comprises ethyl nitrite in a liquid.

\* \* \* \* \*